United States Patent
Sossong et al.

(10) Patent No.: US 10,228,486 B2
(45) Date of Patent: *Mar. 12, 2019

(54) INSPECTION OF OBJECTS BASED ON PRIMARY AND SECONDARY SCANNING

(71) Applicant: Decision Sciences International Corporation, Poway, CA (US)

(72) Inventors: Michael James Sossong, Ramona, CA (US); Shawn McKenney, Ramona, CA (US); Robert Whalen, La Jolla, CA (US); Gary Blanpied, Ramona, CA (US); Andre Lehovich, San Diego, CA (US); Priscilla Kurnadi, San Diego, CA (US)

(73) Assignee: Decision Sciences International Corporation, Poway, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/243,819

(22) Filed: Aug. 22, 2016

(65) Prior Publication Data

US 2016/0356913 A1 Dec. 8, 2016

Related U.S. Application Data

(63) Continuation of application No. 14/423,381, filed as application No. PCT/US2013/056035 on Aug. 21, 2013, now Pat. No. 9,423,362.

(Continued)

(51) Int. Cl.
G01N 23/046 (2018.01)
G01V 5/00 (2006.01)
(Continued)

(52) U.S. Cl.
CPC ......... *G01V 5/0016* (2013.01); *G01N 23/046* (2013.01); *G01N 23/20008* (2013.01); *G01T 1/167* (2013.01)

(58) Field of Classification Search
CPC .... G01J 9/00; G01J 1/4228; G01J 3/02; G01J 3/2803; G01J 3/36
See application file for complete search history.

(56) References Cited

U.S. PATENT DOCUMENTS 7,220,967 B1 5/2007 Shapiro et al.
7,470,905 B1 12/2008 Goldberg et al.
(Continued)

FOREIGN PATENT DOCUMENTS

AU 2007202020 A1 11/2007
JP 2000-235007 A 8/2000
(Continued)

OTHER PUBLICATIONS

Armitage, J., "Cosmic Ray Inspection and Passive Tomography for SNM Detection," International Conference on Applications of Nuclear Techniques, AIP Conference Proceedings, 1194(1):24-35, Dec. 2009.

(Continued)

*Primary Examiner* — David Porta
*Assistant Examiner* — Mamadou Faye
(74) *Attorney, Agent, or Firm* — Perkins Coie LLP

(57) ABSTRACT

Techniques and systems for two scanners to inspect objects based on an initial scanning of all objects and an additional scanning of objects that are determined by the initial scanning to potentially include one or more suspect regions. In one implementation, a system can include a primary scanner for performing the initial or primary scanning and a smaller secondary scanner for the additional or secondary scanning to provide efficient and accurate inspection of objects while maintaining a desired throughput of the inspection. In another implementation, a single scanner can be used to perform both the initial scanning and the additional scanning while maintaining a sufficient throughput of a line of objects under inspection.

29 Claims, 10 Drawing Sheets

Related U.S. Application Data

(60) Provisional application No. 61/691,642, filed on Aug. 21, 2012.

(51) Int. Cl.
*G01N 23/20008* (2018.01)
*G01T 1/167* (2006.01)

(56) References Cited

U.S. PATENT DOCUMENTS

| | | | |
|---|---|---|---|
| 7,945,105 B1 | 5/2011 | Jaenisch | |
| 2006/0284094 A1 | 12/2006 | Inbar | |
| 2007/0278423 A1* | 12/2007 | Eikman | G01T 1/1612 250/484.5 |
| 2008/0191133 A1* | 8/2008 | Morris | G01N 23/20 250/307 |
| 2008/0315091 A1 | 12/2008 | Morris et al. | |
| 2009/0295576 A1 | 12/2009 | Shpantzer et al. | |
| 2010/0032564 A1 | 2/2010 | Morris et al. | |
| 2010/0166605 A1 | 7/2010 | Hamada et al. | |
| 2011/0101230 A1* | 5/2011 | Inbar | G01T 1/167 250/370.05 |

FOREIGN PATENT DOCUMENTS

| | | |
|---|---|---|
| JP | 2009-536322 A | 10/2009 |
| JP | 2010-508521 A | 3/2010 |
| JP | 2010-156602 A | 7/2010 |
| WO | 2008/118209 A2 | 10/2008 |
| WO | 2010/138607 A1 | 12/2010 |

OTHER PUBLICATIONS

Extended Search Report dated Mar. 29, 2016 for European Application No. 13842125.0, filed Aug. 21, 2013 (9 pages).

International Search Report and Written Opinion dated May 12, 2014 for International Application No. PCT/US2013/056035, filed Aug. 21, 2013 (13 pages).

Office Action dated May 23, 2017 for Japanese Patent Application No. 2015-528630, filed Aug. 21, 2013 (7 pages).

* cited by examiner

US 10,228,486 B2

INSPECTION OF OBJECTS BASED ON PRIMARY AND SECONDARY SCANNING

CROSS REFERENCE TO RELATED APPLICATIONS

This patent document is a continuation application of and claims priority to U.S. patent application Ser. No. 14/423,381, filed on Feb. 23, 2015, which is a 371 national stage application of International Patent Application No. PCT/US2013/056035, filed on Aug. 21, 2013, which claims the benefit of priority of U.S. Provisional Patent Application No. 61/691,642, filed on Aug. 21, 2012. The entire contents of the before-mentioned patent applications are incorporated by reference as part of the disclosure of this document.

TECHNICAL FIELD

This patent document relates to particle detection including muon tomography based on cosmic muon rays and applications in inspection of objects, cargos, vehicles, containers and others for various uses, including security and portal monitoring.

BACKGROUND

Materials with high atomic weights such as nuclear materials can be detected by various methods. One notable technology is muon tomography which exploits scattering of highly penetrating cosmic ray-produced muons to perform non-destructive inspection of the material without the use of artificial radiation. The Earth is continuously bombarded by energetic stable particles, mostly protons, coming from deep space. These particles interact with atoms in the upper atmosphere to produce showers of particles that include short-lived pions which decay producing longer-lived muons. Muons interact with matter primarily through the Coulomb force without nuclear interaction. Muons radiate energy much less readily than electrons and lose energy due to scattering through electromagnetic interactions. Consequently, many of the cosmic ray-produced muons arrive at the Earth's surface as highly penetrating charged radiation. The muon flux at sea level is about 1 muon per $cm^2$ per minute.

Muon tomography utilizes cosmic ray-produced muons as probing particles and measures scattering of such muons that penetrate through a target object under inspection. As a muon moves through the material of the target object, Coulomb scattering off of the charges of sub-atomic particles perturb its trajectory. The total deflection depends on several material properties, but the dominant effect is the atomic number, Z, of nuclei. The trajectories are more strongly affected by materials that make good gamma ray shielding (such as lead and tungsten for example) and by special nuclear material (SNM), that is, uranium and plutonium, than by materials that make up more ordinary objects such as water, plastic, aluminum and steel. Each muon carries information about the objects that it has penetrated, and measurements of the scattering of multiple muons can be used to probe the properties of these objects. For example, a material with a high atomic number Z and a high density can be detected and identified when the material is located, inside low-Z and medium-Z matter.

SUMMARY

Techniques and systems for using cosmic ray-produced muons to inspect objects based on an initial scanning of all objects and an additional scanning of objects that are determined by the initial scanning to potentially include one or more suspect regions. In one implementation, a system can include a primary scanner for performing the initial or primary scanning and a smaller secondary scanner for the additional or secondary scanning to provide efficient and accurate inspection of objects while maintaining a desired throughput of the inspection. In another implementation, a single scanner can be used to perform both the initial scanning and the additional scanning while maintaining a sufficient throughput of a line of objects under inspection.

As an example for using both a primary scanner for performing the initial or primary scanning and a secondary scanner for the additional or secondary scanning, a method is disclosed for inspecting objects based on muon tomography using cosmic ray-produced muons and includes operating a first muon tomography scanner that includes position sensitive charged particle detectors to perform an imaging scan of an object under inspection for a first imaging duration to obtain a first muon tomography image of the entire object; processing the first muon tomography image of the entire object to obtain information inside the object; and generating a clearance signal when the processing of the first muon tomography image reveals no suspect region inside the object to set the first muon tomography scanner ready for receiving a next object for inspection. This method further includes, when the processing of the first muon tomography image reveals one or more suspect regions inside the object, removing the object from the first muon tomography scanner to place the object in a second, separate muon tomography scanner to perform an imaging scan of the object for a second imaging duration longer than the first imaging duration to obtain a second muon tomography image of only each suspect region of the object without imaging the entire object, wherein the second muon tomography scanner is configured to have a smaller imaging area covered by the position sensitive charged particle detectors to obtain an image of only a portion of the object; and while the second muon tomography scanner is being operated to further inspect the object with the one or more suspect regions, operating the first muon tomography scanner to receive a next object to inspect.

As an example for a two-scanning system using both a primary scanner for performing the initial or primary scanning and a secondary scanner for the additional or secondary scanning, a system is disclosed for inspecting objects based on muon tomography using cosmic ray-produced muons and includes a main inspection traffic path along which objects under inspection are lined up in sequence to move in a common direction; a first muon tomography scanner located in the main inspection traffic path to inspect the objects in sequence, the first muon tomography scanner configured to include position sensitive charged particle detectors to perform an imaging scan of an object under inspection for a first imaging duration to obtain a first muon tomography image of the object, and the first muon tomography scanner further configured to have a sufficiently large imaging area covered by the position sensitive charged particle detectors to obtain a full image of the entire object; a second, separate muon tomography scanner that includes position sensitive charged particle detectors to perform an imaging scan of the object for a second imaging duration longer than the first imaging duration to obtain a second muon tomography image of only each suspect region of the object without imaging the entire object, wherein the second muon tomography scanner is configured to have a smaller imaging area covered by the position sensitive charged particle detectors to obtain an image of only a portion of the object, and the second muon tomography scanner is located at a second location off the main inspection traffic path without interfering movement of the objects in the main inspection traffic path; and an inspection control mechanism that processes the first muon tomography image of the object, generates a clearance signal when the processing of the first muon tomography image reveals no suspect region inside the object to set the first muon tomography scanner ready for receiving a next object for inspection, and issues an instruction for removing the object from the first muon tomography scanner to place the object in the second muon tomography scanner for further inspection if the first muon tomography image reveals one or more suspect regions inside the object, while operating the first muon tomography scanner to receive a next object to inspect.

In another aspect, this patent document discloses a system for inspecting objects based on two scanners. This system includes a main inspection path along which objects under inspection are lined up in sequence to be inspected; a first scanner located in the main inspection path to inspect the objects in sequence, the first scanner configured to perform a first scan of an object under inspection to obtain information on whether or not the object contains one or more suspect regions that potentially include a threat; a second, separate scanner to perform a second scan of each suspect region within the object that is identified by the first scanner to obtain additional information of each suspect region of the object; and an inspection control mechanism coupled to both the first scanner and the second scanner and configured to process the first scan of the object, to generate a clearance signal when the processing of the first scan reveals no suspect region inside the object to set the first scanner ready for receiving a next object for inspection, and to issue an instruction for removing the object from the main inspection path and placing the removed object into the second scanner for further inspection if the first scan reveals at least one suspect region inside the object, while operating the first scanner to receive a next object in the main inspection path to inspect.

In yet another aspect, a method is disclosed for inspecting objects based on two scanners and includes operating a first scanner to perform a first scan of an object under inspection to obtain information concerning potential presence of one or more suspect regions containing a threat within the object; processing the obtained information from the first scan to generate a clearance signal when the obtained information from the first scan reveals no suspect region inside the object; when the processing of the first scan reveals one or more suspect regions inside the object, removing the object from the first scanner to place the object in a second, separate scanner to perform a second scan of the object to obtain a second scan of each suspect region of the object identified from the first scan produced by the first scanner; and processing the information from the second scanner to make a final decision as to whether the object contains one or more threats.

DETAILED DESCRIPTION

Figure 1A:
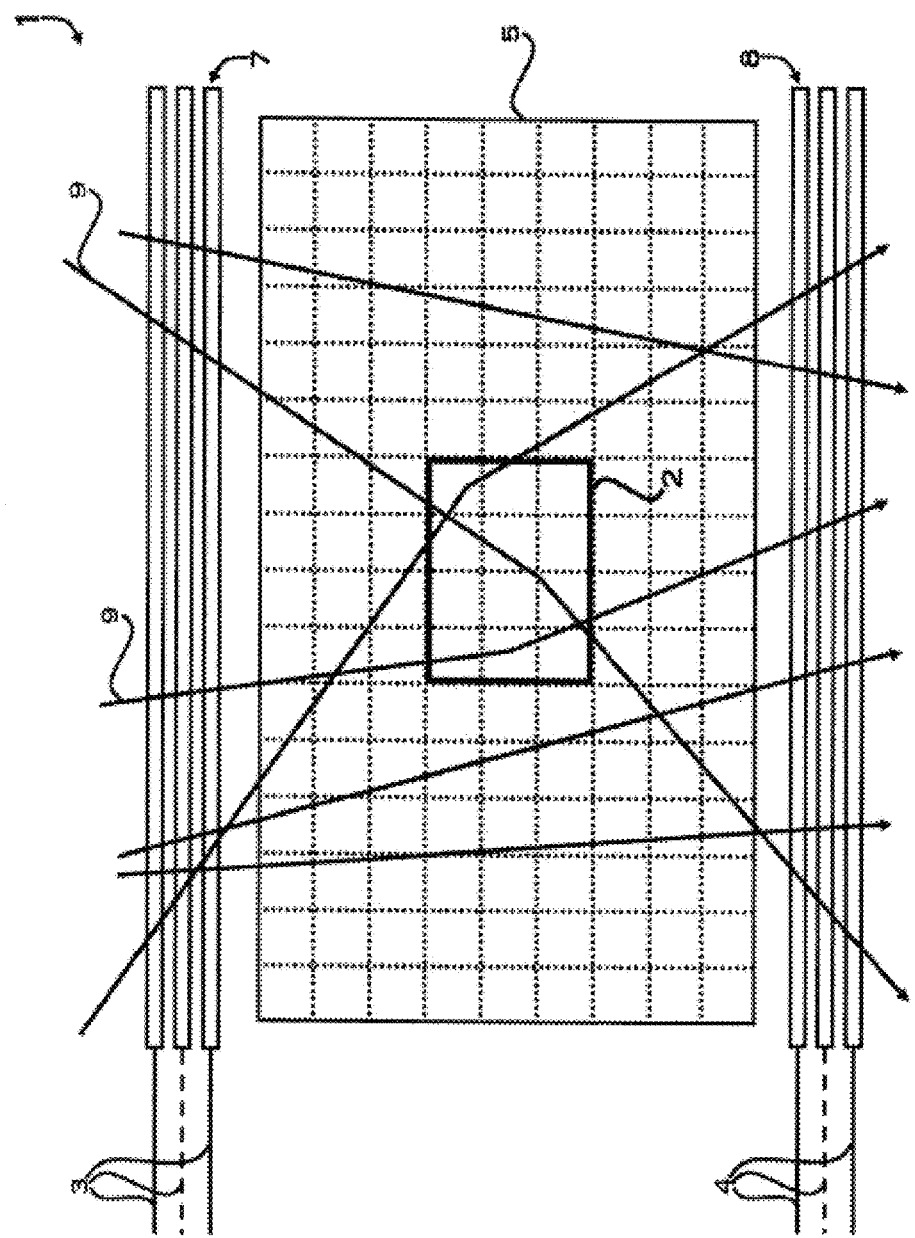
FIG. 1A illustrates an example of a muon tomography scanner system for portal monitoring and other inspection applications utilizing cosmic ray-produced muons to obtain images of an object.

Techniques and systems are disclosed for inspection of objects based on primary scanning and secondary scanning. Two different types of scanner systems can be used to implement the primary scanning and secondary scanning: a first type of inspection systems that include a first primary scanner for performing the initial or primary scanning and a secondary scanner for the additional or secondary scanning as illustrated by examples in FIGS. 3, 4, 5 and 6; and a second type of inspection systems that include a single scanner to perform both the initial scanning and the additional secondary scanning as illustrated by examples in FIGS. 7, 8A and 8B. Both types of systems can be configured and controlled to provide efficient and accurate inspection of objects while maintaining a desired throughput of the inspection.

Muon tomography scanners based on cosmic ray-produced muons rely on the natural density of the muons from the sky that cannot be increased artificially. Therefore, under this limit of incoming muons from the sky, a muon tomography scanner needs to let an object be exposed to the natural influx of muons from the sky for a minimum period of time to ensure that a sufficient number of muons penetrate through and are scattered by the object under inspection to generate a muon tomography image with sufficient details to enable the identification of the object and/or discrimination from the surrounding clutter. This operation is referred to as imaging scanning and the duration of such scanning is dictated by the time of the exposure to muons needed for a particular quality of muon tomography images. Long scanning times provide image details more than images obtained with shorter scanning times. In practical inspection systems, this aspect of the muon tomography scanner imposes a trade-off between the throughput of the inspection and the reliability of the inspection. Some small fraction of vehicles will contain suspect configurations of shielding, radiation emitting materials or other materials increasing suspicions of the presence of a threat. As an example, if 90% of vehicles do not contain suspect configurations and can be cleared in 30 seconds and 10% of vehicles contain suspect configurations requiring a minute to clear, the average throughput is 33 seconds per scan. 10% of scans do continue to 60 seconds, but the average throughput is negligibly affected.

One implementation of such a muon tomography scanner would inspect vehicles one at a time at a vehicle checkpoint, with each vehicle subject to the same scanning time, long enough to provide sufficient image detail to affirmatively discriminate and/or identify nuclear materials (and/or shielding) with a high level of confidence. This can unnecessarily lower the vehicle inspection throughput since a large majority of the vehicles are unlikely to carry suspect nuclear materials and thus do not need to undergo the same level of scrutiny as a few vehicles that may carry suspect shielding or nuclear materials. Such an inspection system is undesirable, particularly at checkpoints with high daily traffic.

The techniques and systems described in this document provide two levels of scanning to maintain a desired traffic flow of objects for inspection. All objects in line for inspection are subject to a first scanning by a muon scanner for a pre-defined short scanning time to determine whether an object contains a suspect region. Only when an object is determined to have one or more suspect regions based on the first scanning, an additional scanning is then performed to make a final determination. Hence, a method for inspecting objects based on tomography using cosmic ray-produced muons is provided to operate a muon tomography scanner that includes position sensitive charged particle detectors to perform an imaging scan of an object in a line of objects under inspection for an imaging duration to obtain a muon tomography image of the entire object. This method processes the muon tomography image of the entire object to obtain information on one or more suspect regions inside the object, and generates a clearance signal when the processing of the muon tomography image reveals no suspect region inside the object to set the muon tomography scanner ready for receiving a next object for inspection. When the processing of the muon tomography image reveals one or more suspect regions inside the object, the muon tomography scanner is operated to scan the object for an additional scan time that is sufficiently long to make an affirmative decision on whether or not the one or more suspect regions inside the object constitute a threat.

In one implementation, the muon tomography scanner would inspect one vehicle at a time with a scan time shorter than the above-described long scan time with a high level of confidence. This shorter scan time can be determined based on circumstances of the application, e.g., the likelihood that a vehicle could conceal a threat. Various simple scenes may not require long scan times to achieve the needed level of confidence to clear. This use of a shorter scan time can increase vehicle inspection throughput of the vehicle checkpoint. Reduction in scan times will result in lower quality images, but such lower quality images can be designed to be sufficient to identify suspect objects or configurations at a pre-defined confidence level. If the confidence level indicating that no potential threat packages are present exceeds a pre-defined confidence requirement to clear, the vehicle is cleared. If not enough information has been collected to provide high confidence that no suspect configurations are present, the scan continues. If suspect configurations are identified, these regions are scanned with an extended scanning time, if needed, to provide a higher quality image allowing either the vehicle to be cleared or a threat to be detected. This extended scanning is performed in a way so as not to significantly affect the vehicle inspection throughput at the checkpoint, with the vehicle made to wait for an opportune time for the extended scan if necessary. This balancing between the inspection throughput and level of confidence can be optimized based on the specific circumstances of a vehicle checkpoint.

In another implementation, two muon tomography scanners can be used at the vehicle checkpoint. The first scanner is operated as the "primary" scanner to scan vehicles with scan times sufficiently short to maintain a desired level of vehicle throughput. The second scanner is operated as the "secondary" scanner to provide additional scanning when needed. For example, if the scan by the first scanner indicates that a vehicle may be suspect, it is then subjected to an extended scanning at the primary scanner location if the traffic flow permits, or at the "secondary" scanner if the first scanner is required to scan the next vehicle in order to maintain the traffic flow, thus unavailable for the extended scanning. The use of two scanners ensures that the desired level of vehicle inspection throughput can be maintained by using the first "primary" scanner to perform the primary scan while at the same time suspect vehicles are scanned by the second scanner to allow threat/no-threat classification with a high level of confidence. The two scanners need not be identical since the secondary scanner may need to scan just a portion of the vehicle where the primary scanner has identified a possible concern. This will allow the detector modules of the secondary scanner to be smaller, thereby reducing the size of the scanner system as a whole and resulting in savings of cost and space. This two-scanner implementation may be used in various applications, including, e.g., checkpoints with a high level of vehicle traffic.

Muon tomography scanners are particle detection devices to detect the presence of certain objects or materials such as nuclear materials and to obtain tomographic information of such objects in various applications including but not limited to inspecting packages, containers, vehicles, boats or aircraft at security check points, border crossings and other locations for nuclear threat objects that may range from fully assembled nuclear weapons to small quantities of highly shielded nuclear materials.

For example, a particle detection system can include an object holding area for placing an object (such as a vehicle, cargo container, or package) to be inspected, a first set of position-sensitive muon detectors located on a first side of the object holding area to measure positions and directions of incident muons towards the object holding area, a second set of position-sensitive muon detectors located on a second side of the object holding area opposite to the first side to measure positions and directions of outgoing muons exiting the object holding area, and a signal processing unit, which may include, e.g., a microprocessor, to receive data of measured signals of the incoming muons from the first set of position sensitive muon detectors and measured signals of the outgoing muons from the second set of position sensitive muon detectors. As an example, each of the first and second sets of particle detectors can be implemented to include drift tubes arranged to allow at least three charged particle positional measurements in a first direction and at least three charged particle positional measurements in a second direction different from the first direction. The signal processing unit is configured to analyze scattering behaviors of the muons caused by materials within the object holding area based on the measured incoming and outgoing positions and directions of muons to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position-sensitive muon detector can be implemented in various configurations, including using drift cells such as drift tubes filled with a gas which can be ionized by muons. Such a system can be used to utilize natural cosmic ray-produced muons for detecting one or more objects in the object holding area.

As will be explained in more detail below, in particular illustrative embodiments, the particle detection systems can utilize drift tubes to enable tracking of charged particles, such as muons, passing through a volume as well as concurrent detection of neutron particles. Such charged particle detectors can be employed in tracking and imaging using charged particles other than those produced by the cosmic rays incident on the earth's atmosphere. In general, these charged particle detectors are applicable to any charged particle from an appropriate source. For example, muons can be produced by cosmic rays or a low intensity beam of muons from an accelerator.

In applications for portal monitoring and other inspection type uses, the illustrative embodiments provide an approach to enabling robust nuclear material detection at a reduced cost and with increased effectiveness. Furthermore, the approach can provide a radiation portal monitor which is capable of determining if a given vehicle or cargo is free of nuclear threats by both measuring the absence of a potential shielded package and the absence of a radiation signature.

The muon tomography scanners of the illustrative embodiments shown in the accompanying drawings employ cosmic ray-produced charged particle tracking with drift tubes. As will be explained in more detail below, the muon tomography scanners can utilize drift tubes to enable tracking of charged particles of different kinds, such as muons, passing through a volume as well as detection of gamma rays by providing a proper gas mixture contained by the drift tubes. Advantageously, these portal monitoring systems can effectively provide the combined function of a cosmic ray radiography apparatus with passive or active gamma radiation counter to provide a robust detector for nuclear threats. This eliminates the need for two separate instruments for sensing muons and gamma rays separately. In implementation of the system, a gamma ray or neutron source can included in the system to enable active rather than only passive interrogation of the vehicle and thereby provide a detectable increase in the gamma ray counting rate.

Tomographic methods, designed to construct an image or model of an object from multiple projections taken from different directions, can be implemented in the cosmic ray system to provide a discrete tomographic reconstruction of the volume of interest based on the data provided by the muons. In some implementations, Monte Carlo simulation techniques can be used to study applications and shorten scanning times. Other stochastic processing methods may also be used in implementing the muon tomographic imaging.

Figure 1B:
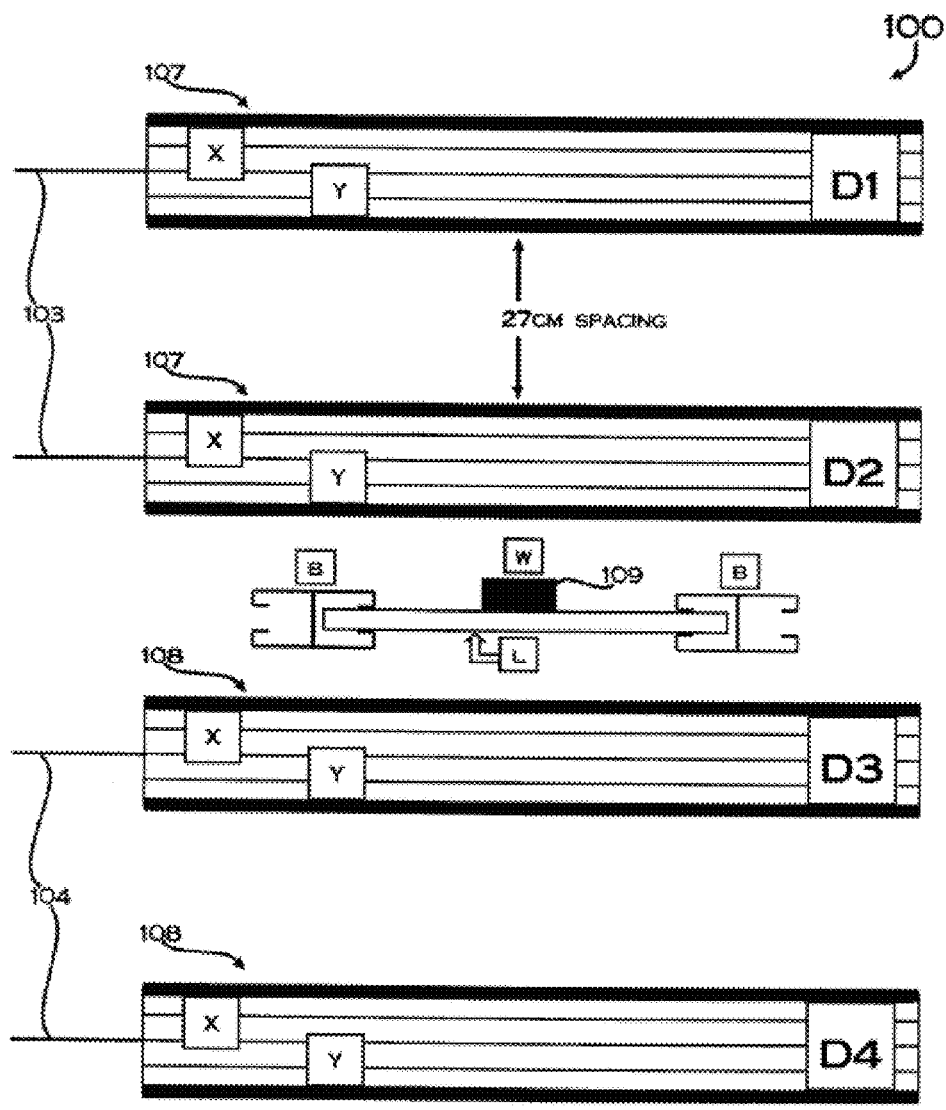
FIG. 1B illustrates a side view of a muon tomography scanner system utilizing cosmic ray-produced muons to detect an object.
Figure 2:
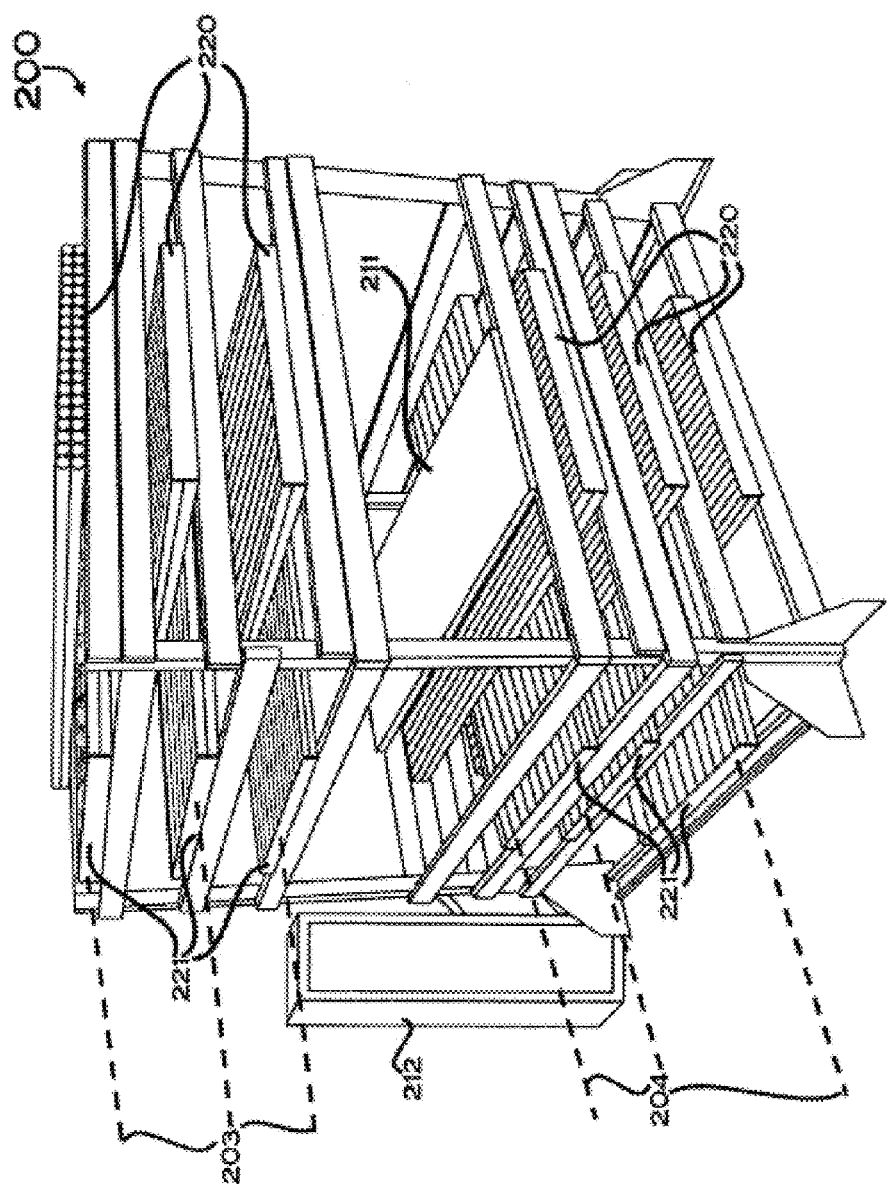
FIG. 2 illustrates a detailed perspective view of a muon tomography scanner system.

The cosmic ray radiography function of the particle detection systems of the embodiments can be more readily understood with reference to examples of detection systems adapted to detect cosmic ray-produced charged particles such as those shown in FIGS. 1A, 1B and 2.

FIG. 1A illustrates a muon detection system utilizing cosmic ray-produced muons to detect an object. The system 1 includes a set of two or more planes 3 of position-sensitive muon detectors 7 arranged above a volume 5 to be imaged for providing the position and angles (i.e., directions in the 3-D space) of incoming muon tracks 9. The muon detectors 7 are configured to measure the position and angles of incoming muon tracks 9 with respect to two different directions, e.g., in two orthogonal coordinates along x and y axes. Muons pass through the volume 5 where the object 2 may be located and are scattered to an extent dependent upon the material 2 occupying the volume through which they pass. Another set of two or more planes 4 of position-sensitive muon detectors 8 are configured to record outgoing muon positions and directions. The drift tubes in detectors 7 and 8 are arranged to allow at least three charged particle positional measurements in a first direction and at least three charged particle positional measurements in a second direction which is different from the first direction and may be orthogonal to the first direction. Side detectors (not shown) may be used to detect more horizontally orientated muon tracks. The scattering angle of each muon is computed from the incoming and outgoing measurements. Each drift tube can include a non-flammable gas, such as a mixture of argon, carbon dioxide and Tetrafluoromethane ($CF_4$).

A signal processing unit, e.g., a computer, is provided in the system 1 to receive data of measured signals of the incoming muons by the detectors 7 and outgoing muons by the detectors 8. This signal processing unit is configured to analyze the scattering of the muons in the volume 5 based on the measured incoming and outgoing positions and directions of muons to obtain a tomographic profile or the spatial distribution of the scattering density reflecting the scattering strength or radiation length within the volume 5. The obtained tomographic profile or the spatial distribution of the scattering density within the volume 5 can reveal the presence or absence of the object 2 in the volume 5. FIG. 1A shows drift tube detectors 7 and 8 are located on top and bottom sides of the volume 5. In some implementations, additional drift tube detectors can be implemented on sides of the volume 5 to form a box or four sided structure into which a package, a vehicle or cargo container can enter for scanning by the system.

The processing of measurements for cosmic ray-produced muons in a volume under inspection (e.g., a package, a container or a vehicle) by the processing unit for the system 1 in FIG. 1A, and other systems described in this application can include reconstructing the trajectory of a charged particle such as a muon through the volume 5, measuring the momentum of an incoming muon based on signals from the detectors 7, measuring the momentum of an outgoing muon based on signals from the detectors 8, and determining the spatial distribution of the scattering density of the volume 5. These and other processing results can be used to construct the tomographic profile and measure various properties of the volume 5.

For example, the reconstruction of the trajectory of a charged particle passing through a detector having a set of drift cells can include (a) obtaining hit signals representing identifiers of drift cells hit by charged particles and corresponding hit times; (b) grouping in-time drift cell hits identified as being associated with a track of a particular charged particle passing through said detector; (c) initially estimating a time zero value for a moment of time at which said particular charged particle hits a drift cell; (d) determining drift radii based on estimates of the time zero values, drift time conversion data and the time of the hit; (e) fitting linear tracks to drift radii corresponding to a particular time zero value; and (f) searching and selecting a time-zero value associated with the best of the track fits performed for a particular charged particle and computing error in time-zero and tracking parameter. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the muon through the apparatus to the nearest few nanoseconds to provide the time-zero.

Also for example, the processing for measuring the momentum of an incoming or outgoing muon based on signals from the detectors can include, for example, (a) configuring a plurality of position sensitive detectors to scatter a charged particle passing there through; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

Also for example, the spatial distribution of the scattering density of the volume can be determined from charged particle tomographic data by: (a) obtaining predetermined charged particle tomography data corresponding to scattering angles and estimated momentum of charged particles passing through object volume; (b) providing the probability distribution of charged particle scattering for use in an expectation maximization (ML/EM) algorithm, the probability distribution being based on a statistical multiple scattering model; (c) determining substantially maximum likelihood estimate of object volume density using the expectation maximization (ML/EM) algorithm; and (d) outputting reconstructed object volume scattering density. The reconstructed object volume scattering density can be used to identify the presence and/or type of object occupying the volume of interest from the reconstructed volume density profile. Various applications include cosmic ray-produced muon tomography for various homeland security inspection applications in which vehicles or cargo can be scanned by a muon tracker.

The tomographic processing part of the signal processing unit may be implemented in a computer at the same location as the detectors 7 and 8. Alternatively, the tomographic processing part of the signal processing unit may be implemented in a remote computer that is connected on a computer network such as a private network or a public network such as the Internet.

Thus, multiple scattering of cosmic ray-produced muons can be used to selectively detect high-Z material in a background of normal cargo. Advantageously, this technique is passive, does not deliver any radiation dose above background, and is selective of high-Z dense materials.

FIG. 1B illustrates a side view of another detection system utilizing cosmic rays to detect an object, the system 100 has two planes 103 of muon detectors 107 located above the sample 109 and two planes 104 of muon detectors 108 located below the sample 109. In the system 100 the two planes of muon detectors in each of 103 and 104 are separated by a spacing of 27 cm.

FIG. 2 illustrates a detailed perspective view of another charged particle detector 200 in which position sensitive detectors 203 are arranged above the sample holder plane 211 and position sensitive detectors 204 are arranged below the sample holder plane 211. Each set of position sensitive detectors comprises a first double-layer 220 of drift tubes 203 or 204 arranged in the X direction and a second double-layer 221 of drift tubes 203 or 204 arranged in the Y direction. In each of the layers 220, 221, the drift tubes 203 or 204 are arranged in two rows, offset by half a tube diameter from each other.

Drift tube modules 203 and 204 are operable to detect both cosmic ray-produced muons and gamma rays. In the system of FIG. 2, the drift tube modules are made up of 12 foot long aluminum drift tubes which are configured to measure the position and angle of incoming and outgoing muon tracks in the X and Y coordinate directions. The aluminum in the detectors provides a considerable amount of mass in which gamma rays and energetic electrons are absorbed or scattered. The energetic electrons produced in these processes are detected locally in the drift tubes in the same way that more energetic cosmic rays are detected.

The tubes can be arranged in different ways. For example, the layers need not have to be 90 degrees from one another, but can be smaller non-zero angles. Also by way of example, the top layer could be at 0 degrees, middle layer at 45 degrees from the first, and a third layer 90 degrees from the first. This would allow resolution of multiple tracks that occur at the same instance of time.

Also, other position sensitive detector arrangements capable of scattering the charged particle passing there through and providing a total of at least three individual positional measurements can be adopted instead of the arrangement of detectors of FIG. 2. At least 3 position measurements are required so as to enable a line fit with a free parameter from which one can track the particle.

In one example implementation, the data acquisition electronics 212 is operably coupled to the drift tubes. Drift tubes of the detector system 200 of FIG. 2 are connected to respective electronic amplifiers (not shown) which increase the voltage of the deposited signal (associated with a cosmic ray-produced muon passing through a drift tube). For each drift channel, the amplified signal is turned into a digital signal with a piece of electronics called a discriminator (on if there is a hit, off if no hit), which preserves the precise time of the hit. This combination of amplifier and discriminator is the "front-end" electronics. The time and channel number that the digital signal is registered to the nearest nanosecond by the time-to-digital-converters (TDCs). Each drift tube has its own front-end electronics and TDC.

The front-end electronics can be custom built for the purpose of processing signals from drift-tubes. Analog-to-digital electronics circuitry identifies current pulses on the wires of the drift-tubes. This circuit converts the pulse to digital levels corresponding to the crossing of current thresholds of the current on the wire. These digital levels are time-tagged in the TDC and delivered to a CPU for further processing. The data is processed to identify the cosmic ray events. Candidate muon-track-events are processed to reconstruct a measured trajectory for the muon as it traversed the detectors. The event data, track data, and pertinent diagnostic data are also stored on the hard drive. The processing of measurements for cosmic ray-produced muons in a volume under inspection (e.g., a package, a container or a vehicle) by the data acquisition unit of the system of FIG. 2, or other signal processing unit linked thereto, can be similar to those explained above for the system of FIG. 1A. For example, processing measurements may be reconstructing the trajectory of a muon through the volume, measuring the momentum of an incoming muon based on signals from the detectors, measuring the momentum of an outgoing muon based on signals from the detectors, and determining the spatial distribution of the scattering density of the volume.

Advantageously, the system 200 in FIG. 2 can selectively detect high density shielding of radioactive material occupying the volume from multiple scattering of the cosmic ray-produced muons whilst also counting gamma rays emitted from the radioactive material. In addition to detecting high density materials, such as lead, gold, tungsten, uranium and plutonium, the system can be employed to detect medium density materials, such as steel, iron and copper, and also low density materials, such as water, plastic, concrete and aluminum, albeit with a somewhat lower accuracy than for high density materials. This capability may allow the scanner to detect, discriminate, and/or identify objects other than nuclear materials and shielding.

Based on the above specific examples on muon tomography scanners, FIGS. 3, 4, 5 and 6 illustrate examples of details in inspection systems and methods for using cosmic ray-produced muons to inspect objects based on a primary scanner and a secondary scanner to provide efficient and accurate inspection of objects while maintaining a desired throughput of the inspection. In various implementations, the secondary scanner is used to perform a focused scanning on one or more areas that are identified to be suspect by the primary scanner and thus can be configured as a smaller scanner as the primary scanner. Also, for checkpoints with low to medium vehicular traffic, a single scanner may be sufficient and the object can be brought back to the single scanner for additional scanning instead of being sent to the secondary scanner.

Figure 3:
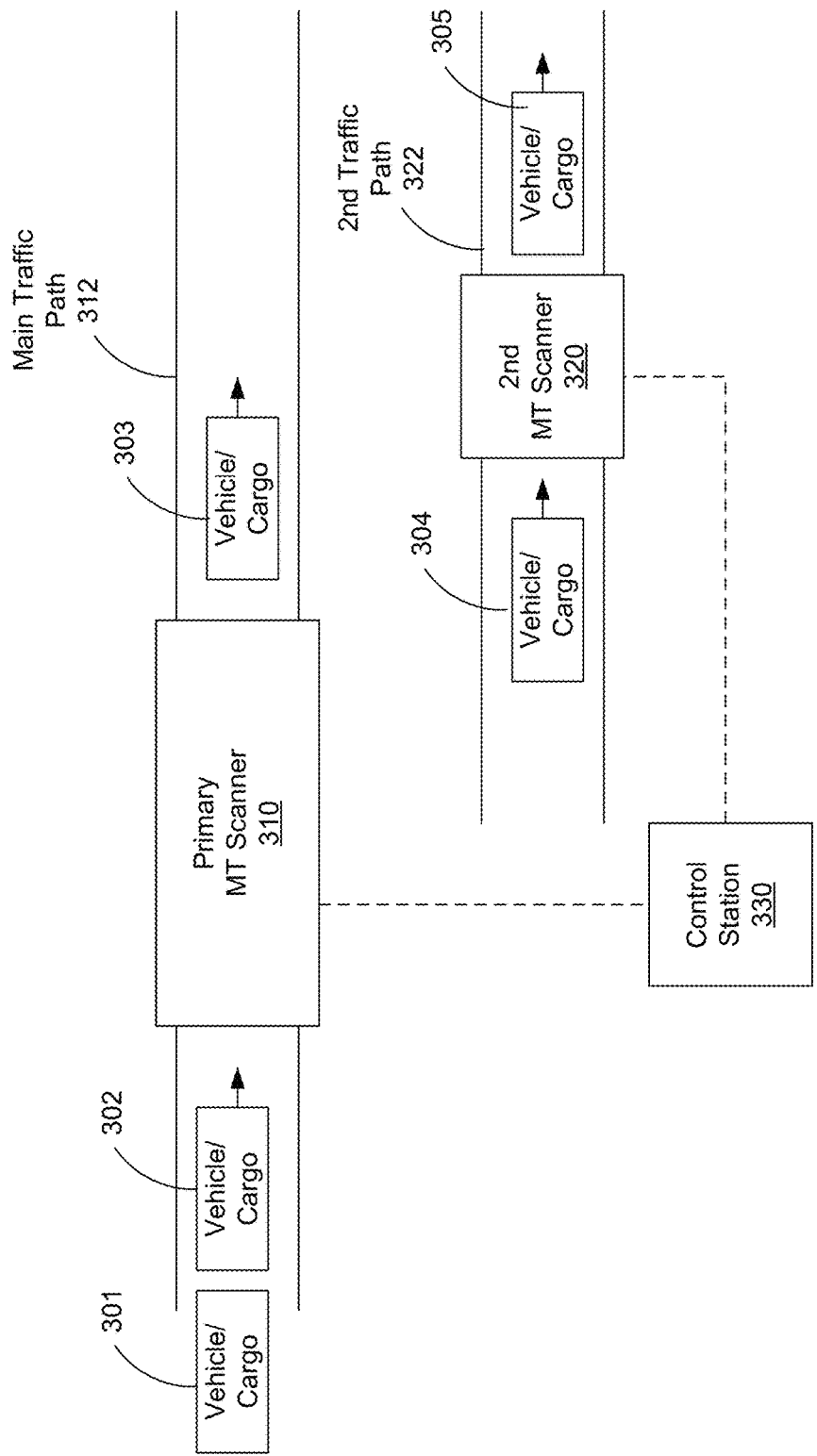
FIG. 3 shows an example of a vehicle inspection system based on a primary muon tomography scanner for an initial scan and for maintaining a flow of vehicles under inspection and a secondary muon tomography scanner that provides off-line detailed scanning over a suspect region identified by the primary scanner.

FIG. 3 shows an example of a vehicle inspection system at a high vehicle traffic checkpoint based on a primary muon tomography scanner for an initial scan and for maintaining a flow of vehicles under inspection and a secondary muon tomography scanner that provides off-line detailed scanning of a suspect region identified by the primary scanner. In FIG. 3, the system includes two muon tomography scanners 310 and 320 that are located at two separated locations. The primary scanner 310 is located in a main inspection traffic path 312 along which vehicles (301, 302, 303, etc.) under inspection are lined up in sequence to move in a common direction from the left side of the primary scanner 310 to the right side. In one embodiment, the primary scanner 310 can be configured to include position sensitive charged particle detectors as shown in FIGS. 1A and 1B to perform an imaging scan of a vehicle under inspection for a first imaging duration to obtain a first muon tomography image of the vehicle. As illustrated, the primary scanner 310 is configured to have a sufficiently large imaging area covered by the position-sensitive charged particle detectors to obtain a full image of the entire vehicle. For low to moderate vehicle traffic checkpoints, the second inspection, if needed, is performed by the first and only scanner 310 at the checkpoint at an opportune time so that the checkpoint traffic is not disturbed. Since the traffic volume in this case is lower, it is anticipated that the second scan can be performed without having the vehicle wait for an unreasonably long time. If possible, extended scanning will be performed at the primary scanner. Transfer to the secondary scanner is determined from traffic flow requirements.

The second scanner 320 in FIG. 3 is a secondary scanner that includes position-sensitive charged particle detectors to perform an imaging scan and is located outside the main traffic path 312 so its operation would not interfere with the traffic flow in the main traffic path 312. As shown in FIG. 3, the second scanner 320 can be placed in a second traffic path 322 for selected vehicles that are determined to need additional scanning based on the initial inspection in the main traffic path 312 by the primary scanner 310. Notably, the second scanner 320 can be configured differently from the primary scanner 310 to provide different imaging capabilities because it serves a very different inspection function from that of the primary scanner 310. In one aspect, the second scanner 320 is configured to perform its scanning for a second imaging duration longer than the first imaging duration performed by the primary scanner 310 to provide more detailed imaging data from the vehicle. As such, the second scanner 320 operates slower than the primary scanner 310. In another aspect, the second scanner 320 is smaller in size to obtain a second muon tomography image of only each suspect region of the vehicle without imaging the entire vehicle. Therefore, the position sensitive charged particle detectors in the second scanner 320 are less in numbers and are used to obtain an image of only a portion of the vehicle. This reduces the size and cost of the second scanner 320. At checkpoints without a second scanner, the first scanner 310 will be used to perform the confirming second scan on a vehicle if needed.

In operation of the system in FIG. 3, the primary scanner 310 performs an inspection on all vehicles to maintain a sufficiently high throughput in the main traffic path 312 for the overall inspection operation. The second smaller scanner 320 permits extended scanning for cases where such scanning interferes with the flow of traffic through the primary inspection station. At checkpoints without a second scanner, the first scanner will be used to perform the confirming slow and detailed extended scan on a vehicle, if needed.

FIG. 3 further shows an inspection control mechanism represented by the control station 330. The control station 330 processes the first muon tomography image of the vehicle from the primary scanner 310 and generates a clearance signal when the processing of the first muon tomography image reveals no suspect region inside the vehicle. If a vehicle is cleared by the primary scanner 310, the primary scanner 310 is set to be ready for receiving a next vehicle for inspection. However, if the scanning by the primary scanner 310 indicates one or more suspect regions in a vehicle, the control station 330 initiates the extended scanning mode for further scanning of the vehicle so indicated. During the extended scanning, traffic waiting to be scanned is evaluated. If such waiting traffic exists, the control station 330 issues an instruction for removing the vehicle from the primary scanner 310 off the main traffic path 312 to place the suspect vehicle in the second scanner 320 for further inspection while operating the primary scanner 310 to continue inspecting the subsequent vehicles that are in line in the main traffic path 312 waiting for inspection. The longer scanning time by the second scanner 320 allows better and more detailed images of each suspect region to be obtained from the suspect vehicle 304. Since the second scanner 320 is operated separately, the slow operation of the second scanner 320 does not slow down the traffic in the main traffic path 310 under the inspection by the primary scanner 310. After inspection by the second scanner 320, a final status of the suspect vehicle 305 is determined: either the suspect vehicle 305 is cleared because the extended scan reveals no threat in the suspect region identified by the primary scanner 310 or the suspect vehicle 305 is indicated by the second scanner 320 to contain suspect materials or devices and will be subject to further processing. At single-scanner checkpoints the control station 330 will direct instead that the vehicle in question be rescanned with the only available scanner at an opportune time when there is minimal impact to checkpoint traffic.

Figure 4:
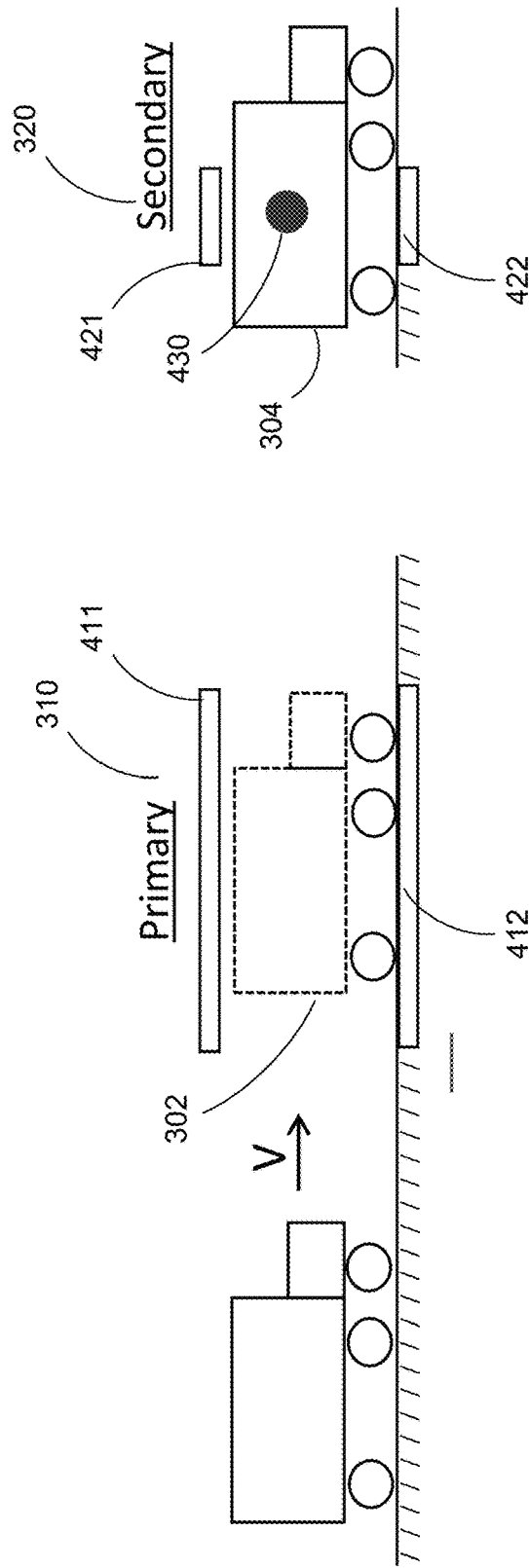
FIG. 4 shows an example of the operation of the primary and secondary scanners in FIG. 3.

FIG. 4 shows an example of the operation of the primary and secondary scanners in FIG. 3. The primary scanner 310 includes top detectors 411 positioned on top of vehicle 302 under inspection and bottom detectors 412 placed on the ground. The vehicle 302 is driven over the bottom detectors 412 during the scanning operation. The secondary scanner 320 similarly includes top detectors 421 positioned on top of vehicle 304 under inspection and bottom detectors 422 placed on the ground. The top and bottom detectors 421 and 422 are much smaller than the top and bottom detectors 411 and 412 of the primary scanner 310 because the secondary scanner 320 is to scrutinize a suspect region 430 within the suspect vehicle 304 that is identified by the primary scanner 310. At single-scanner checkpoints the vehicle 302 will be instead moved back to scanner 310 for the second scan.

Figure 5:
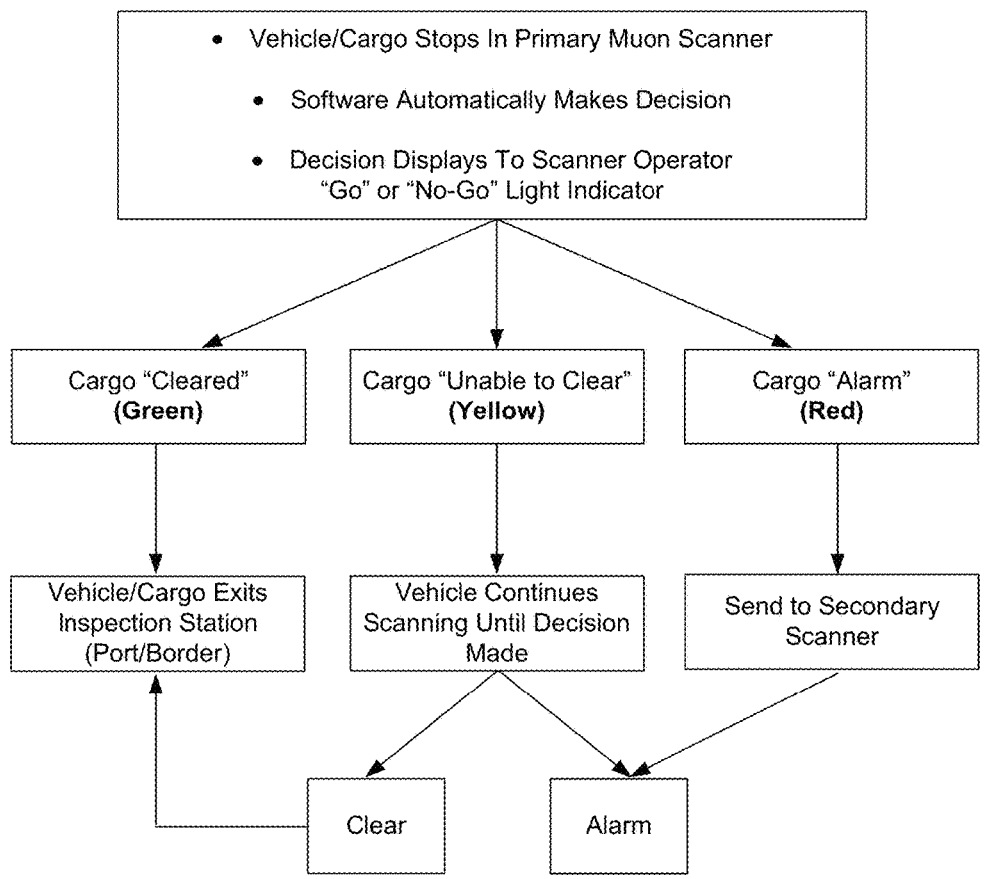
FIG. 5 shows an example of inspection operation details of the system in FIG. 3.

FIG. 5 shows an example of inspection operation details of the system in FIG. 3. In this example, a cargo or vehicle may be subject to further scanning by the primary scanner 310 or the second scanner 320 when the initial scan by the primary scanner 310 is unable to clear the cargo or unclear the cargo. The control station 330 may provide a user interface to generate a cargo "cleared" indicator in green when no suspect region is found by the primary scanning, a cargo "alarm" indicator in red when a suspect region is identified by the primary scanning, or a cargo "unable to clear" indicator in yellow when neither of the above two indicators cannot be generated for some reason. When a cargo "unable to clear" indicator is generated, the vehicle at issue can be held in the primary scanner for further processing or can be sent to the second scanner for further scanning. When a cargo "alarm" indicator is generated, the vehicle at issue is directed to the second scanner for further scanning and inspection.

Figure 6:
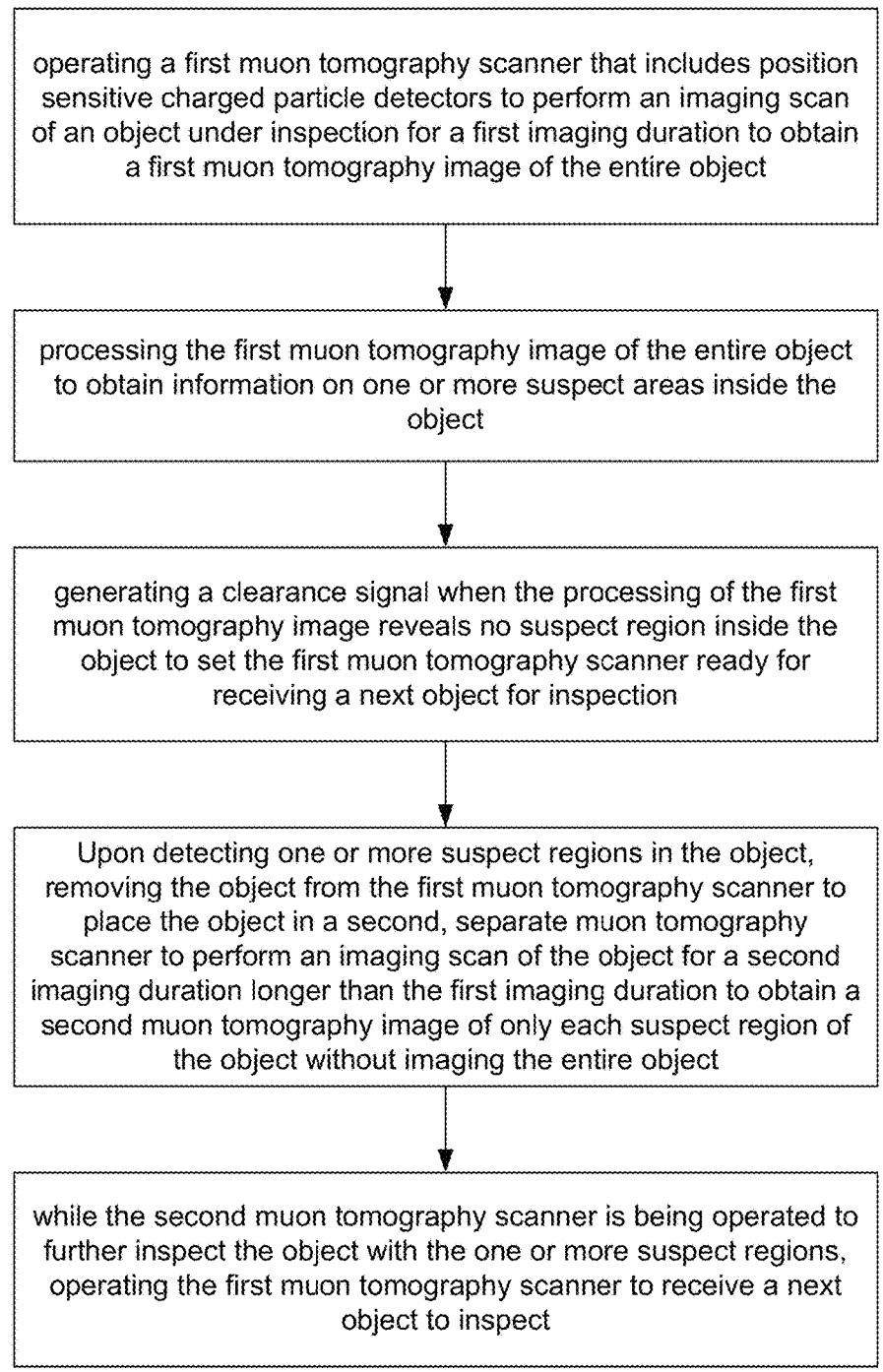
FIG. 6 shows an example of the operational flow based on the system in FIG. 3 or similar systems.

FIG. 6 shows an example of the operational flow based on the system in FIG. 3 or similar systems. This operational flow includes operating a first muon tomography scanner (the primary scanner 310) that includes position sensitive charged particle detectors to perform an imaging scan of an object under inspection for a first imaging duration to obtain a first muon tomography image of the entire object; processing the first muon tomography image of the entire object to obtain information on one or more suspect regions inside the object; generating a clearance signal when the processing of the first muon tomography image reveals no suspect region inside the object to set the first muon tomography scanner ready for receiving a next object for inspection; when the processing of the first muon tomography image reveals one or more suspect regions inside the object, removing the object from the first muon tomography scanner to place the object in a second, separate muon tomography scanner (secondary scanner 320), if available, that includes position sensitive charged particle detectors to perform an imaging scan of the object for a second imaging duration longer than the first imaging duration to obtain a second muon tomography image of only each suspect region of the object without imaging the entire object. While the second muon tomography scanner is being operated to further inspect the object with the one or more suspect regions, the first muon tomography scanner is operated to receive a next object to inspect. At single-scanner checkpoints without the secondary scanner 320, the object is placed back in the primary scanner 310 if a second inspection is desired.

The above performance of additional scanning of an object that may contain one or more suspect regions by using a second scanner may be implemented by using the same scanner. In absence of the second scanner, any additional scanning of an object can cause delay in scanning other objects in line for the inspection. In order to maintain the continuous traffic flow of the objects in line for inspection by the scanner, a different control technique can be applied to minimize the impact to the throughput of the scanner while still allowing performance of the additional scanning.

Figure 7:
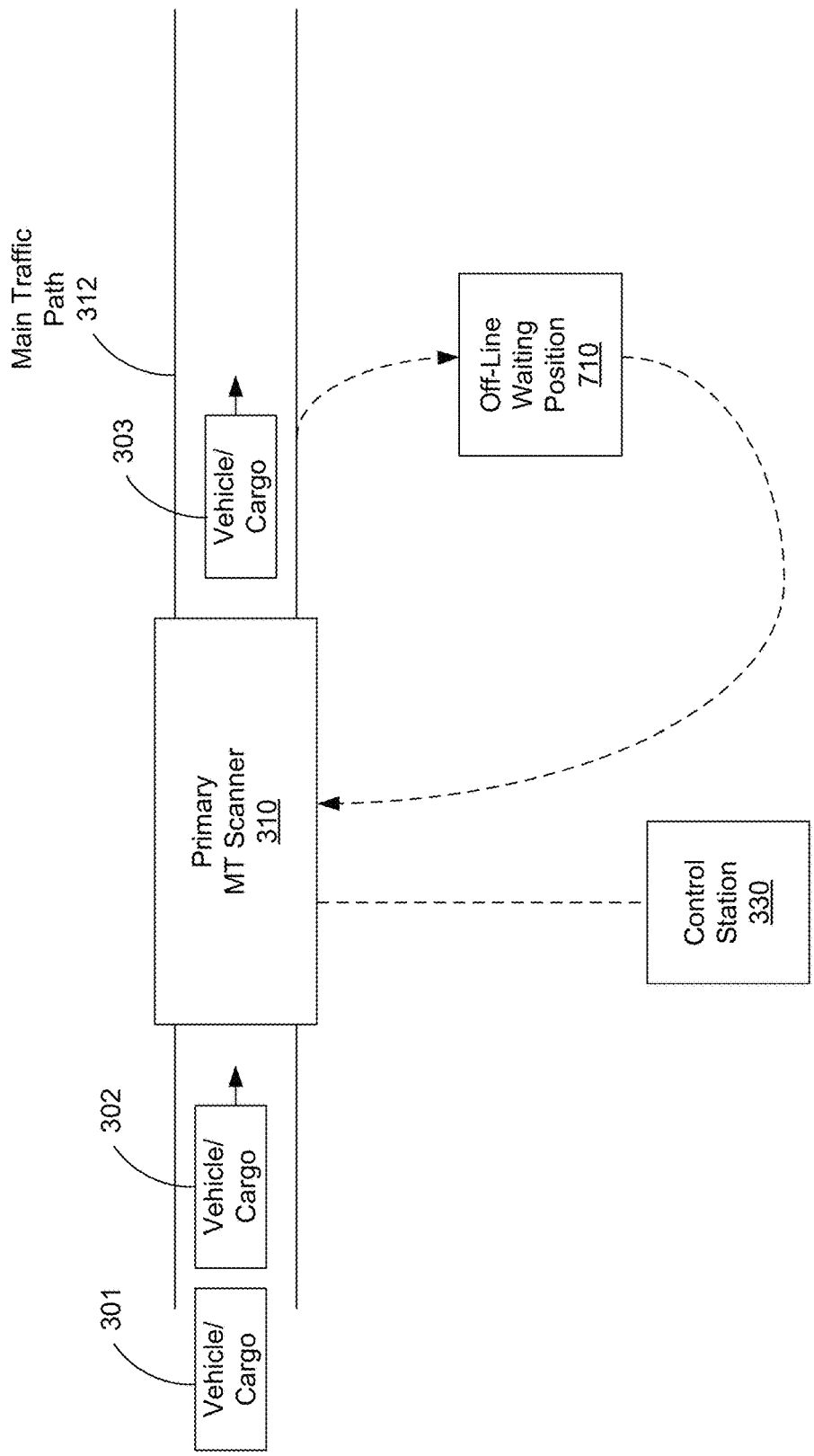
FIG. 7 shows an example of using a single scanner to perform both the initial scanning of all objects in line for inspection and the additional scanning on objects that are determined by the initial scanning to potentially have one or more suspect regions.

FIG. 7 shows an example of a single scanner system for implementing the additional scanning of only objects that fail the initial scanning. In this system, a single scanner 310 is used for all scanning operations without a second scanner. The scanning of the object for the additional scan time is conducted at a later time while placing one or more subsequent objects in the line in the muon tomography scanner 310 to undergo imaging scan without delay. All objects are first subject to the initial scanning by the sole scanner 310. If an object is determined by the initial scanning to be clear of any suspect regions, no additional scanning is performed on that object and the next object in line is moved into the scanner 310 for the initial scanning. If an object is determined to include one or more suspect regions, this object may be moved out of the line of the objects to a waiting position 710 while imaging scan on the one or more subsequent objects in the line continues. After a period of waiting for further inspection when the traffic flow in the line permits, the object in the waiting position is moved back to the muon tomography scanner 310 to complete the scanning of the object for the additional scan time to make an affirmative decision on whether or not the one or more suspect regions inside the object constitute a threat. Depending on the traffic flow condition in the line for the inspection, the additional scanning may be performed on an object without first moving the object out of line.

Figure 8A:
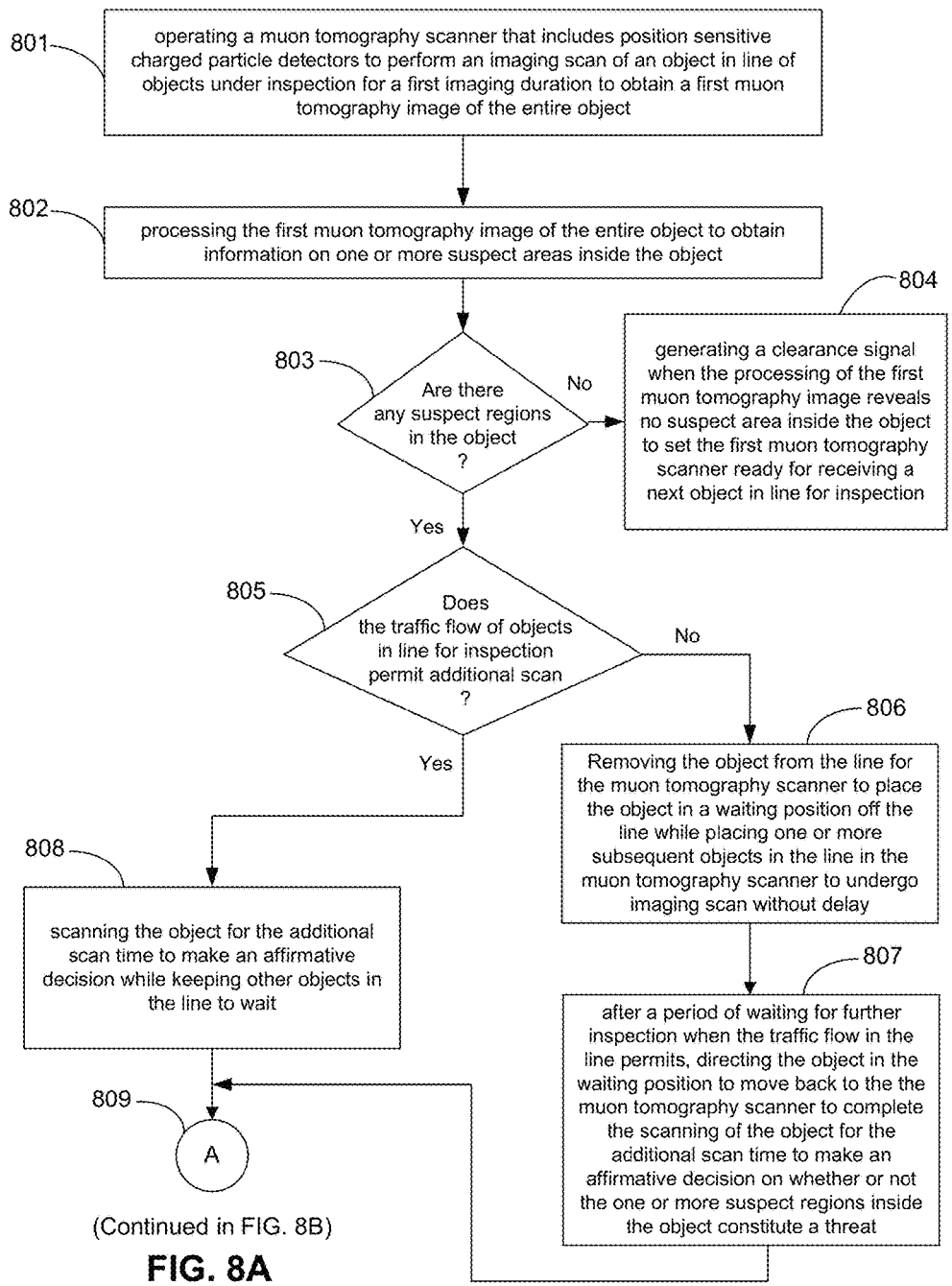
FIGS. 8A and 8B show an example of a scan sequence in performing initial/primary scanning and an additional/secondary scanning.
Figure 8B:
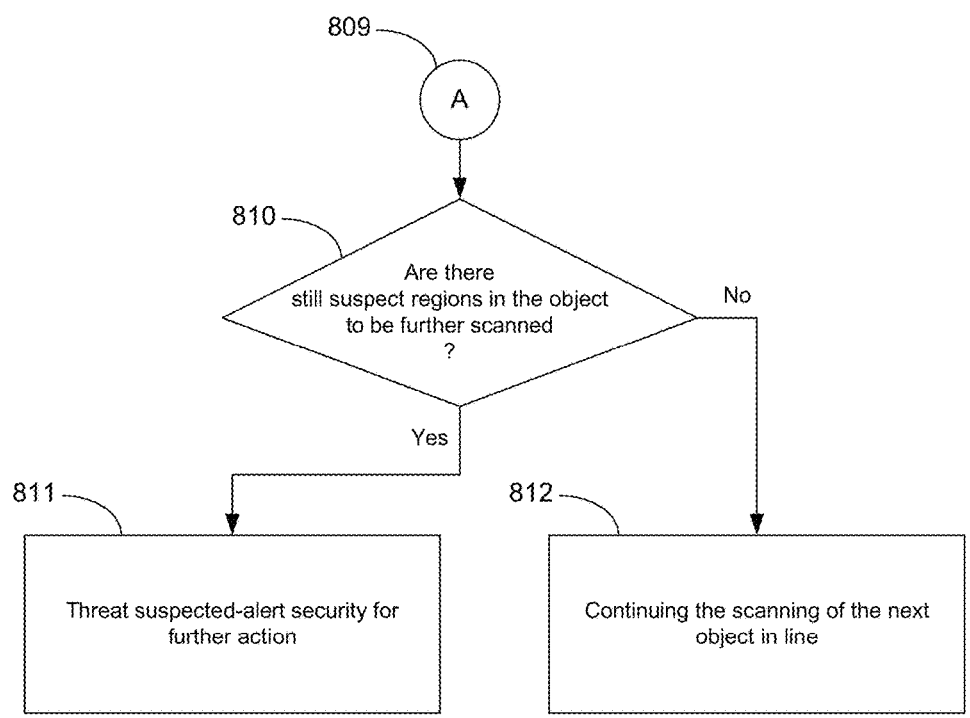

FIGS. 8A and 8B show an example of a scan sequence in performing initial/primary scanning and an additional/secondary scanning by operating a single scanner (such as the system in FIG. 7). At 801, the muon tomography scanner that includes position sensitive charged particle detectors is operated to perform an imaging scan of an object in line of objects under inspection for a first imaging duration to obtain a first muon tomography image of the entire object. At 802, the first muon tomography image of the entire object is processed to obtain information on one or more suspect areas inside the object. If no suspect regions are detected, a clearance signal is generated (803 and 804). If one or more suspect regions are detected, the traffic flow condition at the scanner is determined to see or evaluate whether an additional scan can be performed (803 and 805). If the traffic condition does not permit the additional scan, the object is removed from the line and is placed in a waiting period (see FIG. 7) while other objects in line are continued to be scanned without delay and an affirmative decision is made on the object (806 and 807). If the traffic condition permits the additional scan, the object is kept at the scanner for the additional scan while subsequent objects line are kept in line waiting (808). Next at 810, if there is one or more suspect regions in the object, a threat is suspected and an alert is generated for the security to take further action, e.g., removing the object off line to further investigate the suspected object while allowing the scanner to continue scanning the next object in line (811).

Referring back to FIG. 3, the system concept for vehicle inspection can be implemented to other inspection systems such as an automated inspection system similar to the airport luggage carousels where the objects under inspection are placed on a carriage belt to move the objects through the primary scanner 310. When an object is determined by the primary scanner to be a suspect, the object is removed from the carriage belt to the secondary scanner 320 for further inspection and processing.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or a variation of a sub combination.

Only a few implementations are disclosed. Variations and enhancements of the described implementations and other implementations can be made based on what is described and illustrated in this document.

What is claimed is:

1. A method for inspecting objects based on two scanners, comprising:
    operating a first scanner to perform a first scan of an object under inspection to obtain information concerning potential presence of one or more suspect regions containing a threat within the object;
    processing the obtained information from the first scan to generate a clearance signal when the obtained information from the first scan reveals no suspect region inside the object;
    when the processing of the first scan reveals one or more suspect regions inside the object;
        obtaining information on a flow of objects to be inspected by the first scanner,
        determining that the first scanner is unavailable for performing an additional scan of the object based on the first scanner being required to scan a next object to maintain the flow of objects under inspection, and
        removing, after the determining, the object from the first scanner to place the object in a second smaller scanner to perform a second scan of only a portion of the object corresponding to the one or more suspect regions identified from the first scan produced by the first scanner, wherein the second scanner is configured to have a scan volume of sufficient size to scan each suspect region of the object;
    configuring the second scanner to include a muon tomography scanner that detects an interaction between a natural influx of muons and the object to construct, as part of the second scan, a muon tomography profile of each suspect region identified from the first scan produced by the first scanner; and
    processing the muon tomography profile of each suspect region constructed by the second scanner to make a final decision as to whether the object contains one or more threats.

2. The method as in claim 1, comprising:
    including the first and second scanners as part of a vehicle or cargo inspection system wherein the first scanner is placed in a main traffic path in which vehicles or cargos to be inspected are lined up to pass through the scanner one at a time, and the second scanner is placed off the main traffic path; and
    directing a vehicle or cargo in the main traffic path, that has been determined to include one or more suspect regions by the first scanner, to leave the main traffic path and to enter the second scanner for further inspection while continuing operating the first scanner to inspect subsequent vehicles or cargos in the main traffic path.

3. The method as in claim 1, further comprising:
    configuring the first scanner to include a muon tomography scanner that detects muons interacting with the object to construct a muon tomography profile that is capable of indicating one or more suspect regions potentially containing a threat.

4. The method as in claim 3, further comprising:
    operating the second scanner to detect a radiation or charged particles from the portion of the object as part of the second scan, wherein the radiation or charged particles from the object detected by the second scanner are different from muons.

5. The method as in claim 4, further comprising:
    operating the second scanner to detect electrons, neutrons or gamma rays from the portion of the object as part of the second scan.

6. The method as in claim 3, further comprising:
    configuring the first scanner to detect, in addition to muons, a radiation or charged particles from the object that are different from muons.

7. The method as in claim 6, wherein:
    the radiation or charged particles from the object that are different from muons detected by the first scanner include electrons, neutrons or gamma rays from the object as part of the second scan.

8. The method as in claim 1, wherein the radiation or charged particles from the object detected by the first scanner are different from muons.

9. The method as in claim 8, further comprising:
    operating the first scanner to detect electrons, neutrons or gamma rays from the object as part of the first scan.

10. The method as in claim 1, further comprising:
    configuring the second scanner to detect, in addition to detection of muons, a radiation or charged particles from the portion of the object that are different from muons, as part of the second scan.

11. The method as in claim 10, wherein the radiation or charged particles from the portion of the object that are different from muons detected by the second scanner include electrons, neutrons or gamma rays from the object.

12. The method as in claim 1, further comprising:
    configuring the first scanner to further deliver information on a location of a suspect region within the object to the second scanner.

13. The method as in claim 1, comprising:
    operating the second scanner to obtain more details of each suspect region from the second scan that are not available from the first scan.

14. The method as in claim 1, comprising:
    operating the second scanner to obtain a second image in a duration longer than a duration for operating the first scanner in obtaining a first image.

15. The method as in claim 1, wherein:
    the second scanner is operated to scan only a suspect region within the portion of the object that is identified by processing the first scan from the first scanner.

16. A system for inspecting objects based on two scanners, comprising:
    a main inspection path along which objects under inspection are lined up in sequence to be inspected;

a first scanner located in the main inspection path to inspect the objects in sequence, the first scanner configured to perform a first scan of an object under inspection to obtain information on whether or not the object contains one or more suspect regions that potentially include a threat;

a second smaller scanner to perform a second scan of only a portion of the object corresponding to the one or more suspect regions identified by the first scanner to obtain additional information of each suspect region of the object, wherein the second scanner is configured to have a scan volume of sufficient size to scan each suspect region of the object; and an inspection control mechanism coupled to both the first scanner and the second scanner and configured to:

obtain information on a flow of objects to be inspected by the first scanner in the main inspection path, process the first scan of the object, to generate a clearance signal when the processing of the first scan reveals no suspect region inside the object to set the first scanner ready for receiving a next object for inspection, and issue an instruction to remove the object from the main inspection path and to place the removed object into the second scanner for further inspection if the first scan reveals at least one suspect region inside the object, while operating the first scanner to receive a next object in the main inspection path to inspect, wherein the second scanner includes a muon tomography scanner that detects an interaction between a natural influx of muons and the object to construct, as part of the second scan, a muon tomography profile of a suspect region that is configured to make a final decision as to whether the suspect region contains a threat, and wherein the object is removed from the main inspection path to be placed in the second scanner based on the first scanner being required to scan a next object to maintain the flow of objects under inspection.

17. The system as in claim 16, wherein the second scanner is located at a second location off the main inspection path without interfering movement of the object in the main inspection path.

18. The system as in claim 16, wherein:
the first scanner includes a muon tomography scanner that detects muons interacting with the object to construct a muon tomography profile that is capable of indicating one or more suspect regions potentially containing a threat; and
the second scanner is capable of detecting a radiation or charged particles from the portion of the object as part of the second scan, wherein the radiation or charged particles from the object detected by the second scanner are different from muons.

19. The system as in claim 18, wherein:
the second scanner is capable of detecting electrons, neutrons or gamma rays from the portion of the object as part of the second scan.

20. The system as in claim 18, wherein:
the first scanner detects, in addition to muons, a radiation or charged particles from the object that are different from muons.

21. The system as in claim 16, wherein
the first scanner is capable of detecting a radiation or charged particles from the object as part of the first scan, wherein the radiation or charged particles from the object detected by the first scanner are different from muons.

22. The system as in claim 21, wherein:
the first scanner is capable of detecting electrons, neutrons, or gamma rays from the object as part of the first scan.

23. The system as in claim 16, wherein;
the first scanner is configured to deliver location information of a suspect region within the object to the second scanner.

24. The system as in claim 16, wherein:
the inspection control mechanism is configured to, based on the obtained information on the flow, determine whether to hold the object at the first scanner to perform a further scanning of the object in the first scanner if the first scan reveals one or more suspect regions inside the object.

25. The system as in claim 24, wherein:
when the obtained information on the flow indicates a low to medium flow of objects to be inspected, the inspection control mechanism is configured to hold the object at the scanner to perform a further scanning of the object in the first scanner if the first scan reveals at least one suspect region inside the object.

26. The system as in claim 16, wherein:
one scanner of the first or second scanner includes:
a first set of position sensitive charged particle detectors located on a first side of an object holding area to measure positions and directions of incident charged particles towards the object holding area;
a second set of position sensitive charged particle detectors located on a second side of the object holding area opposite to the first side to measure positions and directions of outgoing charged particles exiting the object holding area; and
a signal processing unit to receive data of measured signals of the incoming charged particles from the first set of position sensitive charged particle detectors and measured signals of the outgoing charged particles from the second set of position sensitive charged particle detectors, wherein the signal processing unit is configured to analyze scattering of the charged particles in the materials within the object holding area based on the measured incoming and outgoing positions and directions of charged particles to obtain a tomographic profile or the spatial distribution of scattering centers within the object holding area.

27. The system as in claim 26, wherein:
the scanner having the first and second sets of position sensitive charged particle detectors is configured to:
reconstruct a trajectory of a muon through the object based on signals from the position sensitive charged particle detectors;
measure an incoming momentum and an outgoing momentum of a muon based on signals from the position sensitive charged particle detectors;
determine a spatial distribution of a scattering density within the object; and
using information of the trajectory, momentum and spatial distribution of the scattering density in the object to construct a tomographic profile inside the object.

28. The system as in claim 26, wherein:
the scanner having the first and second sets of position sensitive charged particle detectors is combined with a passive radiation counter to provide a robust detector for nuclear threats.

29. The system as in claim 26, wherein:
the scanner having the first and second sets of position sensitive charged particle detectors is combined with an active radiation counter to provide a robust detector for nuclear threats.

* * * * *